United States Patent [19]

Galaj

[11] Patent Number: 4,647,376
[45] Date of Patent: Mar. 3, 1987

[54] DEVICE FOR REMOVING THE LIQUID PHASE FROM A SUSPENSION

[75] Inventor: Stanislas Galaj, Arcueil, France

[73] Assignee: Compagnie Generale d'Electricite, Paris, France

[21] Appl. No.: 754,113

[22] Filed: Jul. 12, 1985

[30] Foreign Application Priority Data

Jul. 17, 1984 [FR] France .................... 84 11298

[51] Int. Cl.⁴ ............................................. B01D 33/02
[52] U.S. Cl. ................................ 210/297; 210/257.2; 210/360.1; 210/510.1; 210/512.1; 210/433.2
[58] Field of Search ................ 210/297, 433.2, 321.1, 210/257.2, 360.1, 512.1, 510.1, 780–782, 256, 359

[56] References Cited

U.S. PATENT DOCUMENTS

| 3,788,470 | 1/1974 | Pelmulder et al. | 210/785 |
| 4,040,965 | 8/1977 | Kohlheb | 210/297 |
| 4,093,552 | 6/1978 | Guyer | 210/297 |
| 4,160,738 | 7/1979 | Guter | 210/433.2 |

FOREIGN PATENT DOCUMENTS

| 1482987 | 4/1967 | France . | |
| 56-7606 | 1/1981 | Japan | 210/433.2 |
| 2003054 | 3/1979 | United Kingdom | 210/321.1 |

*Primary Examiner*—Benoit Castel
*Attorney, Agent, or Firm*—Sughrue, Mion, Zinn, Macpeak, and Seas

[57] ABSTRACT

A device for abstracting the liquid phase from a suspension comprises a microporous membrane (23) applied on the outside of a microporous body (22) to which a flat capillary duct (11, 18) is fixed. Means (9) are provided to rotate the duct about a vertical axis, with the membrane being immersed in the suspension in such a manner as to provide tangential filtering of the suspension and to cause the liquid phase filling the duct after passing through the membrane and the porous body to be ejected centrifugally and received by a receptacle (5) provided for the purpose.

8 Claims, 1 Drawing Figure

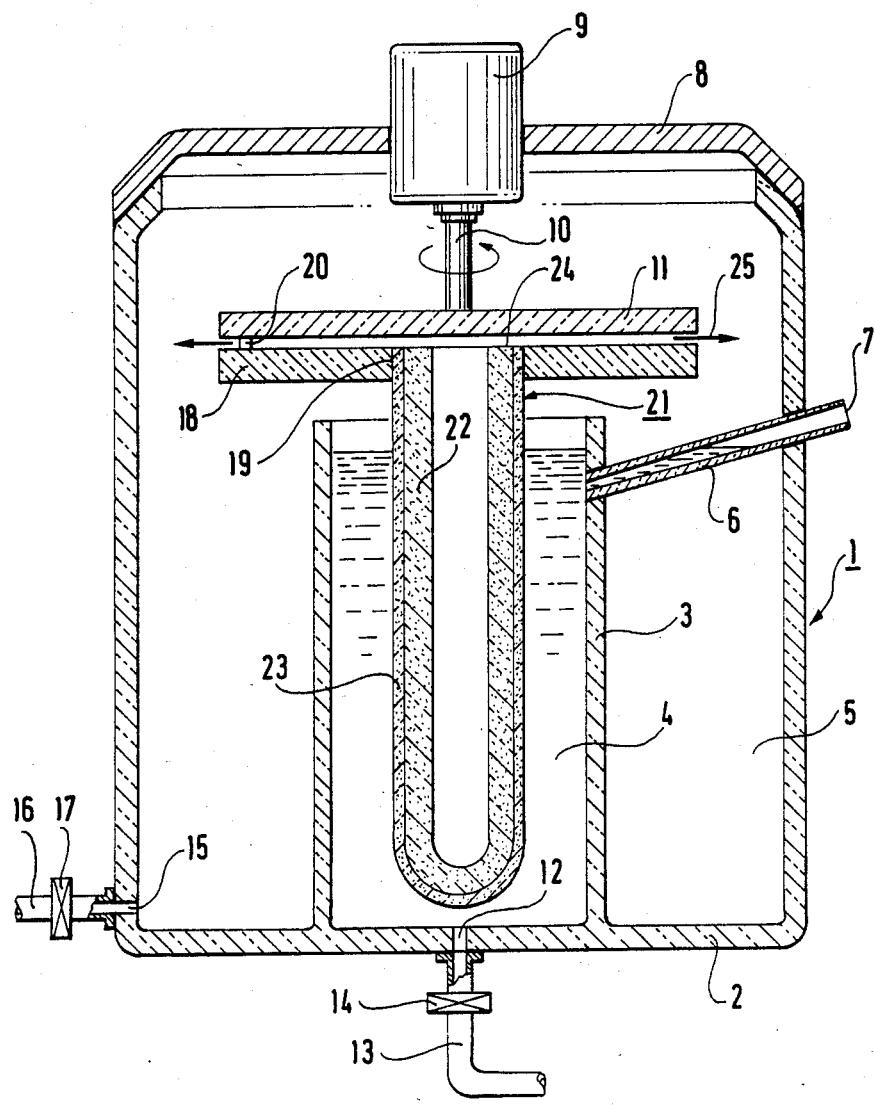

DEVICE FOR REMOVING THE LIQUID PHASE FROM A SUSPENSION

The present invention relates to a device for removing the liquid phase from a suspension.

FIELD OF THE INVENTION

The invention relates to a device for removing the liquid phase from a suspension, the device being of the type comprising:

a microporous tube-shaped membrane disposed along an axis, the pores of said membrane being smaller than the solid particles in the suspension;

a macroporous body having pores which are larger than the particles in the suspension, said body being fixed to said membrane and having an outer surface applied to the inner surface of the membrane, the outer surface of the membrane being in contact with the suspension; and means for creating relative tangential flow between the suspension and the membrane by rotation about said axis.

BACKGROUND OF THE INVENTION

One such device is described in published French patent specification No. 1 564 995 (see, in particular, page 13 left-hand column line 43 to page 14 left-hand column line 24, and FIG. 6). In this prior device, the suspension whose liquid phase is to be extracted is injected under pressure into a cylindrical body 221 and is brought into contact with the outer surface of the membrane constituted by a filter cloth 277 applied against a cylindrical metal mesh 270 disposed coaxially inside the body 221. This prior device further includes a cylindrical mesh 282 disposed coaxially inside the space lying between the membrane and the cylindrical body, which mesh is rotated about the axis in order to cause the suspension to rotate relative to the membrane.

This prior device suffers from the drawbacks of being complex and bulky. Pump means are required to inject the suspension into the cylindrical body under pressure. Further, pressurized backwash means are required to remove solid particles from the suspension after they have accumulated on the outside of the membrane.

Preferred embodiments of the present invention provide a compact device for extracting the liquid phase from a suspension.

SUMMARY OF THE INVENTION

The invention provides a device for extracting the liquid phase from a suspension of the type specified above, which device includes the improvements whereby:

the membrane-forming tube is closed at a first one of its ends and is open at a second one of its ends, the membrane being partially immersed in the suspension in such a manner that the outer surface of at least said first end is in contact with the suspension, said second end being outside said suspension; and the device further includes:

a capillary duct whose inner surface is wettable by the liquid phase of the suspension, said duct including a first opening in which an end portion of the microporous body situated at said second end of the tube is received, said duct including a second opening opening-out outside the suspension, a portion of the liquid phase of the suspension passing through the membrane by capillarity and then filling the pores of the macroporous body and the inside volume of the capillary duct;

means for removing the liquid phase which fills the inside volume of the duct via the second opening from the duct; and a receptacle so disposed relative to said second opening from said duct as to receive the liquid phase ejected therefrom.

In a preferred embodiment of the device, the duct is fixed relative to the membrane and is disposed in a plane perpendicular to the membrane axis in such a manner that the distance of said second opening from the membrane axis is greater than the distance of said membrane from said axis, and the said means for creating a tangential flow of the suspension relative to the membrane by rotation about the axis are means for rotating the duct about the axis, said rotation causing the liquid phase of the suspension filling the inside volume of the duct to be ejected from the second opening of the duct by centrifuging. In this embodiment, the capillary duct may be constituted by two parallel disks which are fixed a small distance apart from each other in parallel with said plane, one of the disks including a central circular bore constituting said first opening, the inside surface of the duct being constituted by the facing plane surfaces of the disks, and the second opening being constituted by the gap between said plane surfaces at the periphery of the disks.

In another embodiment of the device, the membrane axis is substantially perpendicular to the equilibrium surface of the suspension.

In another embodiment of the device, the macroporous embodiment occupies the entire inside volume of the membrane.

In another embodiment of the device, the macroporous body is tubular in shape and closed at one end.

In another embodiment of the device the membrane and the macroporous body are constituted by a single ceramic part.

In another embodiment of the device, the said means for causing the suspension to flow tangentially relative to the membrane by rotation about the axis are means for driving the suspension in rotation relative to the membrane, and the said means for ejecting the liquid phase which fills the inside volume of the duct via the second opening from the duct comprise means for setting up reduced gas pressure at the output from the capillary duct.

BRIEF DESCRIPTION OF THE DRAWING

Embodiments of the invention are described by way of example with reference to the sole FIGURE of the accompanying drawing, which is an axial cross-section through one specific embodiment of the invention.

MORE DETAILED DESCRIPTION

In the FIGURE, a vertical axis cylindrical glass receptacle is given the reference 1. A coaxial inner cylindrical wall 3 is fixed to the bottom 2 of the receptacle 1, and the height of said wall is less than the height of the outer cylindrical wall of the receptacle 1. The inner wall 3 divides the inside volume of the receptacle 1 into an axial chamber 4 and a peripheral chamber 5, which chambers are coaxial. A feed channel 6 passes through the inner wall 3 near the top of the axial chamber 4 and also through the outer cylindrical wall of the receptacle 1. The channel 6 is substantially rectilinear and is inclined relative to the horizontal in such a manner as to allow a liquid to flow into the axial chamber 4 from the free end 7 of the feed channel.

The portion of the bottom of the receptacle 1 located within the axial chamber 4 is pierced at 12 substantially on the axis of the receptacle 1. A drain channel 13 fitted with a valve 14 is connected to the axial chamber thereby. The outer cylindrical wall of the receptacle 1 is also pierced at 15 close to the bottom 2. An evacuation channel 16 fitted with a valve 17 communicates with the peripheral chamber thereby.

A removable stainless steel cover 8 has its rim resting on the top edge of the outer cylindrical wall of the receptacle 1 in such a manner as to close its upper opening. A central opening through the lid 8 engages the outer surface of an electric motor 9 in such a manner as to enable the shaft 10 of the motor 9 to be disposed vertically inside the receptacle 1.

A glass disk 11 is disposed horizontally above the top edge of the inner wall 3 and is fixed coaxially on the free end of the shaft 10. A second glass disk 18 is disposed coaxially with the first disk 11 a little way from the plane face of the disk 11 which faces away from the shaft 10. The second disk 18 has a central coaxial opening 19. The disk 18 is fixed to the disk 11 by three fixing tabs such as 20 disposed at 120° intervals around the periphery of said disks.

One end of a filter having an overall reference 21 is disposed in the opening 19 of the second disk 18. The filter 21 comprises a macroporous body 22 in the form of a tube which is closed at one end. The body 22 may be constituted, for example, from a porous ceramic with the size of its pores being considerably greater than the size of the solid particles in the suspension to be filtered. The entire outer surface of the body 22 is pressed against the inside surface of a microporous membrane 23 which is also in the shape of a tube which is closed at one end. The membrane 23 is also made of porous ceramic and the size of its pores is less than the size of the solid particles to be filtered from the suspension. Preferably, the membrane 23 and the body 22 are constituted by a single filter member 21. As can be seen in the FIGURE, the cylindrical rim of the membrane 23 adjacent the opening to the tubular filter 21 is fixed coaxially in the opening 19 to the disk 18, while the closed bottom end of the tubular filter 21 is located in the axially chamber 4 at a short distance from the bottom 2 of the receptacle 1.

The device described above and shown in the FIGURE operates as follows.

The motor 9 is started in order to rotate the disk 11 together with the membrane 23 and the body 22. The lid 8 is placed on the receptacle 1 so that the axis of the membrane is substantially vertical. Then a suspension to be filtered is poured into the axial chamber 4 from the end 7 of the channel 6 in such a manner that the suspension to be filtered occupies the space between the inner wall 3 and the membrane 23. A tangential flow is thus established of the suspension relative to the membrane once the suspension comes into contact with the membrane.

It is not advisable to insert the membrane into the suspension prior to setting the membrane in rotation, since that would cause the membrane to be clogged up very quickly.

The liquid of the suspension passes through the pores of the membrane 23 and fills of the macroporous body 22 by virtue of capillarity, and rises in the body 22 up to its to end 24, whereas the solid particles in the suspension remain outside the membrane.

In order to obtain this result, the speed of rotation must be less than a limiting speed which would set up a centrifugal force in the suspension opposing capillary suction through the membrane. This limiting speed depends on the outside diameter of the disks 11 and 18, on the size of the pores in the membrane, and in the macroporous body, and on the distance between the disks 11 and 18.

The facing faces of the glass disks 11 and 18 are not smooth so as to ensure that these faces are wettable by the liquid phase of the suspension. Further, the distance between these phases is very small so as to form a capillary duct there between which is flat having an inlet constituted by the opening 19 through the disk 18 and having an outlet which is constituted by the surface delimiting the space between said faces around the periphery of the disks. The liquid phase of the suspension which fills the pores of the macroporous body at its top end 24 is to be found at the inlet to this duct and thus fills the capillay space between the two disks 11 and 18 by virtue of the capillary effect.

The liquid phase filling the inside volume of the duct is centrifuged radially out from the flat duct along the direction of an arrow 25 by virtue of the rotation caused by the motor 9. The outside diameter of the flat duct must necessarily be greater than the outside diameter of the tubular membrane. Since the maximum speed of rotation is limited by the need to allow capillary suction to take place, the suction force round the internal face of the membrane may be increased by increasing the diameter of the flat duct.

The ejected liquid phase strikes the outer wall of the receptacle 1 and flows down to the bottom of the peripheral chamber 5 therein. The liquid phase collected in this manner may be removed from the device by flowing down the channel 16 via the whole 15 and the valve 17. The residue of the suspension may be drained from the chamber 4 via the hole 12, the valve 14 (after opening) and the pipe 13.

The rotary motion of the membrane relative to the suspension provides tangential flow of the suspension relative to the membrane, it also serves to redistribute the solid particles in the suspension in such a manner as to maintain a substantially uniform particle concentration throughout the suspension by virtue of a shear effect, together with turbulence in some cases. Particles therefore do not accumulate on the outer face of the membrane, which therefore does not become clogged.

The beginning of filtering automatically engaged by capillarity, so there is no need, in general, to apply pressure upstream from the device. Nor is there any need to provide a backwash system for unclogging the membrane.

An important advantage of devices in accordance with the invention is that they are compact. Such a device comprises: a filter member including the filter, the ejection duct, and the drive motor in a first assembly; and a second assembly constituted by a receptacle for recovering the filtrate, which receptacle may be much smaller than that shown in the FIGURE.

Another advantage of devices in accordance with the invention is that they enable the liquid phase to be extracted from a small volume of suspension. Such devices may therefore be used for extracting liquid samples for analysis, e.g. from a sample of blood serum.

However, the invention may also be used for filtering larger quantities of liquid suspension, e.g. for filtering water, by using the embodiment shown in the FIGURE.

Naturally the invention is not limited to this embodiment which is being given merely by way of example. In particular, the suspension may be driven to rotate about the membrane while the membrane remains fixed. In such a case the means for ejecting the liquid phase from the second opening of the duct may include the application of reduced gas pressure to the output from the capillary duct.

Further, the macroporous body may be generally cylindrical in shape and may fill the entire inside volume of the membrane.

By way of example, the macroporous body may be made of ceramic material having an outside diameter of 2 mm to 3 mm, a height of 10 mm to 20 mm and a porosity of 10% to 20%, with the pore size being from 10 $\mu$m to 20 $\mu$m. The membrane, also made of ceramic, may be 10 $\mu$m to 30 $\mu$m thick, with a porosity of 30% to 40% and with a pore size of 0.2 $\mu$m to 1 $\mu$m. The speed of rotation of the filter may be about 3,000 rpm. The distance between the two disks constituting the flat duct may be 10 $\mu$m to 100 $\mu$m.

I claim:

1. A device for removing the liquid phase from a suspension containing solid particles, the device comprising:

a microporous tube-shaped membrane disposed along an axis, the pores of said membrane being smaller than the solid particles in the suspension;

macroporous body having pores which are larger than the particles in the suspension, said body being fixed to said membrane and having an outer surface applied to the inner surface of the membrane, the outer surface of the membrane being in contact with the suspension; and means for creating relative tangential flow between the suspension and the membrane by rotation about said axis, which device includes the improvements whereby:

the membrane-forming tube is closed at a first one its ends and is open at a second one of its ends, the membrane being partially immersed in the suspension in such a manner that the outer surface of at least said first end is in contact with the suspension, said second end being outside said suspension;

and the device further includes:

a capillary duct whose inner surface is wettable by the liquid phase of the suspension, said duct including a first opening in which an end portion of the microporous body situated at said second end of the tube is received, said duct including a second opening opening out outside the suspension, a portion of the liquid phase of the suspension passing through the membrane by capillarity and then filling the pores of the macroporous body and the inside volume of the capillary duct, said duct being fixed relative to the membrane and being disposed in a plane perpendicular to the membrane axis in such a manner that the distance of said second opening from the membrane axis is greater than the distance of said membrane from said axis, said capillary duct being constituted by two parallel disks which are fixed a small distance apart from each other in parallel with said plane, one of the disks including a central circular bore constituting said first opening, the inside surface of the duct being constituted by the facing plane surfaces of the disks;

means for ejecting the liquid phase which fills the inside volume of the duct via the second opening from the duct; and a receptacle so disposed relative to said second opening from said duct as to receive the liquid phase ejected therefrom.

2. A device according to claim 1, wherein the said means for creating a tangential flow of the suspension relative to the membrane by rotation about the axis are means for rotating the duct about the axis, said rotation causing the liquid phase of the suspension filling the inside volume of the duct to be ejected from the second opening of the duct by centrifuging.

3. A device according to claim 2, wherein the second opening is constituted by the gap between said plane surfaces at the periphery of the disks.

4. A device according to claim 1, wherein the membrane axis is substantially perpendicular to the equilibrium surface of the suspension.

5. A device according to claim 1, wherein the macroporous body occupies the entire inside volume of the membrane.

6. A device according to claim 1, wherein the macroporous body is tubular in shape and closed at one end.

7. A device according to claim 1, wherein the membrane and the macroporous body are constituted by a single ceramic part.

8. A device according to claim 1, wherein the said means for causing the suspension to flow tangentially relative to the membrane by rotation about the axis are means for driving the suspension in rotation relative to the membrane, and the said means for ejecting the liquid phase which fills the inside volume of the duct via the second opening from the duct comprise means for setting up reduced gas pressure at the output from the capillary duct.

* * * * *